US006618544B1

(12) United States Patent
Bodkin, Sr.

(10) Patent No.: US 6,618,544 B1
(45) Date of Patent: Sep. 9, 2003

(54) FIBEROPTICS PROTECTIVE EMISSION CONTROL

(76) Inventor: Lawrence E. Bodkin, Sr., 1149 Molokai Rd., Jacksonville, FL (US) 32216

( * ) Notice: Subject to any disclaimer, the term of this patent is extended or adjusted under 35 U.S.C. 154(b) by 0 days.

(21) Appl. No.: 10/074,361

(22) Filed: Feb. 12, 2002

(51) Int. Cl.$^7$ .................................................. G02B 6/00
(52) U.S. Cl. .................... 385/147; 385/117; 385/12; 606/15
(58) Field of Search ................ 385/12, 13, 88, 385/92, 94, 117, 118, 902; 362/551–558, 572–575; 606/15, 16; 250/205

(56) References Cited

U.S. PATENT DOCUMENTS 5,334,183 A * 8/1994 Wuchinich .................... 606/46
2002/0071626 A1 * 6/2002 Davis et al. .................. 385/12

* cited by examiner

Primary Examiner—Hemang Sanghavi
Assistant Examiner—Scott Knauss
(74) Attorney, Agent, or Firm—Arthur G. Yeager

(57) ABSTRACT

The invention provides automatic protection from heat damage due to continuing emissions from the distal ends of untended fiberoptics lighting cables, especially those employed in surgical procedures. Damage from such intense and concentrated emissions may include burning of patient tissues, cloth, polymer sheeting and other heat sensitive materials. A simplified proximity detection circuit permits emissions only when an electrically conductive distal terminal or attached implement is purposely held by an operator. Sensitivity is adjusted to provide that casual contact of the small area of the terminal surface at the distal end of the cable with a portion of the human body or other source of substantial earth-ground capacitance, insulated by a nonconductive covering, will not initiate emissions. Emissions can be instantly initiated when wanted by direct contact or by a surgically gloved hand that holds the small terminal with sufficient pressure to maximize the proximity of hand and terminal surfaces. Once distal contact surface is increased by the attachment of a conductive implement, increased pressure is no longer required and emissions can be continued by ordinary handling pressures applied to the implement with surgically gloved hands. With implement detached and cable put aside, the reduction to the relatively small conductive surface of the distal terminal again reduces sensitivity and emissions from the terminal are protectively interrupted. Emissions are controlled either by control of power to the light source or by control of a light blocking element.

11 Claims, 1 Drawing Sheet

FIBEROPTICS PROTECTIVE EMISSION CONTROL

CROSS REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX."

Not applicable

BACKGROUND OF THE INVENTION

1. Field of the Invention

This invention relates to methods and devices intended to provide automatic protection from heat damage to tissues and materials which can result from the continuation of emissions from untended fiberoptics cables. Priorities often demand the casual placement of these cables, once they are detached from surgical implements and the like, and their distal ends may often rest on heat sensitive materials laid over portions of the human body to shield them from possibly damaging substances and/or to isolate them from sterile operating areas.

2. Background Information

The automatic control of hazardous emissions from the distal end of untended fiberoptics cables once they have been detached from implements such as used in surgical procedures, has been accomplished. Typically this has been by means which includes an autoclavable distal terminal that is divided to form two electrical contacts. These contacts are connected to a light control means by two narrow gauge wires included in the fiber bundle of the cable. Attachment of a conductive implement to the terminal completes the circuit to initiate emissions and detachment breaks the circuit to interrupt emissions.

BRIEF SUMMARY OF THE INVENTION

In the applicant's invention, the complexity and expense of an autoclavable, divided distal terminal is avoided. Conventional distal terminals may be used without modification other than their contact with the single narrow gauge wire, which is included in the fiber bundle of the cable and is preferably comparable in diameter to the fibers of the bundle. The wire connects the distal terminal with the proximal terminal which in turn is connected to the sensing terminal of a special proximity control circuit.

The applicant's proximity control circuit is considered special, partly because it requires relatively few components to provide a stable, simply adjustable sensitivity to capacitive influence provided by substantial conductive masses through the earth-ground capacitance effect but there are functioning differences as well.

Like conventional proximity sensing circuits, the applicant's circuit's sensor permits triggering by both direct contact and near contact with substantial conductive masses. However, In the more conventional circuits tested, triggering is largely dependent on the areas of both surfaces involved. In the applicant's circuit, while near contacts are affected by the extent of sensor area, direct contact is independent of surface areas and the circuit may be triggered by hand or other body part contact with no more than a narrow gauge sensing wire, which has a minimal area of sensing surface.

Also, while the conventional circuits tested and the applicant's are triggered by direct sensor contact with a resistively coupled source of household a.c current, the applicant's circuit is also triggered by a direct earth ground connection while the conventional circuits are not.

This proximity circuit is made to protectively interrupt the emissions from the distal end of a fiberoptics cable connected to a light source when the cable is disconnected from an implement using the light source, such as a surgical illuminating and viewing device. This is accomplished without breaking contacts of a control circuit as in other devices.

The applicant's sensing circuit is adjusted so that direct body contact with the small metallic terminal at the distal end of the cable will initiate emission, but a casual contact with electrically shielded surfaces of the body will not. However, sensitivity is also such that a part of the body such as the hand, when electrically shielded by a surgical glove, can initiate emission by squeezing the terminal. This maximizes the proximity of the hand to the terminal by increasing the area of its proximity, removing any air spaces that might exist in the glove and perhaps even temporarily diminishing the thickness of glove material to a slight degree.

When a conductive implement is attached to the terminal the sensing surface is automatically increased so that pressures associated with normal manipulation of the implement is sufficient to maintain emissions. When the implement is removed and the cable set aside, the relatively small surface area is insufficient to cause the proximity sensing circuit to continue the emissions, even when resting on a large but shielded conductive mass, and the emissions are protectively interrupted.

DETAILED DESCRIPTION OF THE INVENTION

The applicant's special proximity sensing circuit requires only five components.
1. A relay to turn the light source on and off. Alternatively, an electrically actuated device to block and unblock light from the source. Prototype coil resistance about 3900 ohms.
2. A full-wave rectifier bridge which has its a.c. terminals connected to the a.c power source and in series with the a.c. coil of the relay or of the alternative electrically actuated light blocking device.
3. A sensitive gate silicon controlled rectifier (SCR) of a type requiring a maximum gate current (Igt) of 200 microamperes or less, having its anode and cathode connected to the d.c. terminals of the rectifier bridge.
4. A large value capacitor, preferably electrolytic, connected to the d.c. terminals of the rectifier bridge in parallel with the SCR.
5. A large value resistance to protectively limit potential current flow from the gate of the SCR to the accessible terminals of the fiberoptics cable and to adjust circuit sensitivity.

The applicant's circuit takes advantage of SCR characteristics that exist under the conditions of low-load in the circuit as shown. Low-load is this context is a load typified by the load of the relay coil, the electromagnetic actuator of a light blocking element or the primary of a transformer supplying lower voltage to some other light blocking device requiring little energy. Even with the SCR of the prototype having a forward current rating of 10 amperes, and the bridge a rating of 1.5 amperes, a larger but still small resistive load such as a 15 watt incandescent bulb caused the circuit to lose sensitivity and a 60 watt incandescent bulb caused the circuit to turn on when energized and latch or maintain the on-state without the control option of an off-state. This would appear to preclude use of the circuit in a directly connected control of a light source requiring current of any substantial magnitude.

Increasing the value of the capacitor can cause a delay in the turn-off time which could be useful in instances where continuation of illumination needs to be maintained when hand proximity may have occasion to be briefly interrupted in the manipulation of an attached implement. The capacitor can be increased to approximately 10 mfd to achieve a turn-off delay of several seconds, but increases beyond this value may result in having the circuit latch, or delay its turn-off indefinitely.

The protection that the circuit provides can be made readily available for use with existing fiberoptics light devices by -adding the proximity control as a plug-in device to be connected between the receptacle of the power source and the plug of the fiberoptics lighting devices, and replacement of the conventional cable with a fiberoptics cable having wire connected terminals, and having its proximal terminal connected to the sensing terminal of the plug-in proximity control.

The protection that the circuit provides can also be made available as an addition to existing fiberoptics lighting devices without connecting the proximity control between the lighting device and its power source. When the sensor control employs a light blocking device in place of the power control of the relay, The proximity control circuit may be powered independently and attached to a special fiberoptics cable which includes a controllable light blocking device at its proximal terminal as well its wire connected proximal and distal terminals and is made to fit in place of the conventional cable.

An object of this invention is to provide a simple, positive protection of materials and patient tissues from heat damage resulting from the intense and concentrated emissions that issue from untended fiberoptics cables that are set aside following removal of attached implements such as those employed during surgery.

An associated object is to provide such protection from unwanted or hazardous emissions from fiberoptics cables in a way that requires the least modification of conventional equipment.

Another associated object is to provide this protection at the least possible expense.

Still another object is to provide protection that is automatic so that no operator attention is required.

Yet another object is to provide this protection without compromising the ability of the fiberoptics cable to be autoclaved in a sterilization process.

An additional object is to provide this protection by means of removable attachments, that modify existing equipment, so that such equipment may be used with or without the protection as a user option, according to purpose and need.

DETAILED DESCRIPTION OF THE PREFERRED EMBODIMENTS

Figure 1:
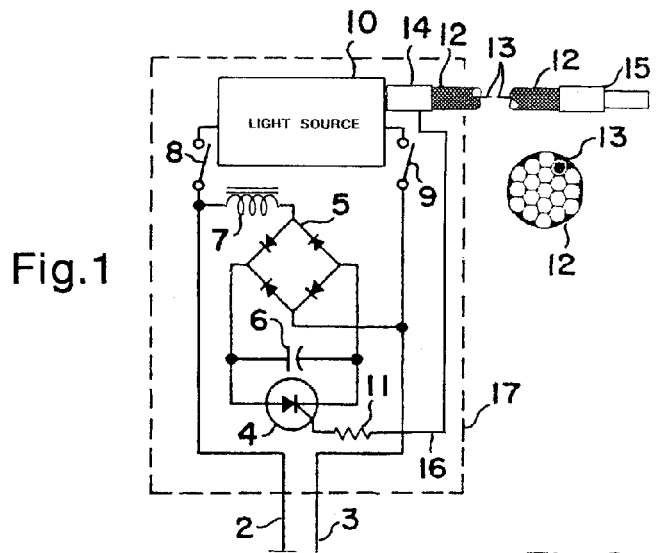
FIG. 1 is a schematic of the proximity control circuit, included in an enclosure with the light source, depicted as being connected to a fiberoptics cable which includes a narrow gauge wire in its fiber bundle that connects its proximal terminal with its distal terminal. The cable is shown is an interrupted side view and in a cross-section in which the included wire, preferably bare, is shown dark among light fibers but outlined in white for contrast.

In FIG. 1, the proximity control circuit is depicted as included within a cabinet enclosure 17 that also houses the light source 10. The circuit, as shown, includes the full-wave rectifier diode bridge 5, with a.c. terminals connected, in series with the relay coil 7, between grounded neutral lead 2 and ungrounded lead 3 that are connected to alternating current power source 1. The coil 7 is shown connected between the bridge 5 grounded neutral lead 2 and it is important that it be connected here and not between the bridge and the ungrounded lead 3 to assure a stable performance.

Silicon controlled rectifier 4 is shown connected across the d.c. output terminals of bridge 5 in parallel with the electrolytic capacitor 6. Capacitor 6 maintains a uniform and stable on-state when the sensitive gate of SCR 4 (less than 200 microamperes lgt) is triggered by contact with sensor lead 16 which is coupled to the gate of SCR 4 by current limiting high value resistance 11. The value of resistance 11, typically and in the prototype, is approximately 12 megohms and can be made substantially more without compromising function.

SCR 4 is triggered into forward conduction when a sufficient source of earth-ground capacitance closely approaches or directly contacts sensor lead 16. Such earth ground capacitance serves to apply a minute triggering signal to the gate. Direct contact with a source of a.c. current has much the same effect. This circuit is also triggered by direct connection to a source of earth ground. Conventional proximity circuits tested were similarly triggered by a resistively coupled connection with the ungrounded side of an a.c. line. However, the commercially available units tested lacked the ability to be triggered by a direct connection to the grounded neutral or earth ground.

Once triggered into conduction, a direct current flow through SCR 4 permits alternating current to flow through relay coil 7 which energizes relay coil 7 and closes normally open contacts 8 and 9, which then supply current to light source 10 from leads 2 and 3 respectively which are connected to the power source 1. This current will continue to be supplied as long as the coil 7 is energized by a source of earth-ground capacitance that is detected by sensor lead 16. When this signal from the sensor lead 16 no longer triggers SCR 4 into forward conduction, relay coil 7 is no longer energized and contacts 8 and 9 open to break both sides of the line and interrupt current flow to the light source from a.c. power source 1. It should be understood that while relay coil 11 of an electromagnetic relay is shown, a common equivalent such as a solid state relay could be substituted.

The sensor lead 16 is connected to the proximal terminal 14 of fiberoptics cable 12 and by means of a narrow gauge wire 13, preferably of a diameter similar to the diameter of fibers in the fiberoptics bundle, as shown in cross section, also connected to the distal terminal 15 of fiberoptics cable. 12. Sensitivity of the circuit can be adjusted by changing the value of sensor ,coupling resistor 11. It has been found that contact with the small distal terminal 15, by a surgically gloved hand, or any other potential earth-ground influence that is similarly shielded, will not cause a turn-on of the light source 10 by a properly adjusted circuit. However, a purposeful, relatively tight gripping of the terminal 15, by such a gloved hand, can effect a turn-on of the light source 10 by increasing the area of close proximity, pressing out any air in the area of gripping, and perhaps even by reducing the degree of separation by slightly and temporarily pressure-thinning the glove material. Once a conductive instrument is attached to the distal terminal 15, the increased conductive surface availability makes it possible for the surgically gloved hand to maintain triggering with hand pressures normally encountered in manipulation of the instrument.

Capacitor 6 typically has a value of 1 to 1.5 microfarads but Increasing the value to as much as 10 mfd can cause delay of turn-off by several seconds. This is useful when it is anticipated that manipulation of the attached instrument will suffer brief handling irregularities that could briefly reduce the triggering proximity to a dangerously low level. Increasing the value of capacitor 6 beyond the 10 mfd level increases a risk of latching, in which the SCR 4 ignores the lack of a triggering signal, resists turn-off and continues to conduct, to energize coil 7 and to thus supply power to the light source indefinitely.

The sensor lead must transmit a bidirectional sensing current to the gate of the SCR 4. While rectifier diodes are often used to protect the gate they cannot be used in this circuit. However, the gate of SCR 4 is well protected by its high resistance coupling to the sensor lead 16 by resistor 11 . Trigger diodes are also quite often included in the gate connection to improve triggering characteristics. While the applicant's circuit will tolerate the inclusion of a trigger diode in the gate connection, triggering without this additional component is crisp and sure and inclusion of a trigger diode is considered superfluous.

Figure 2:
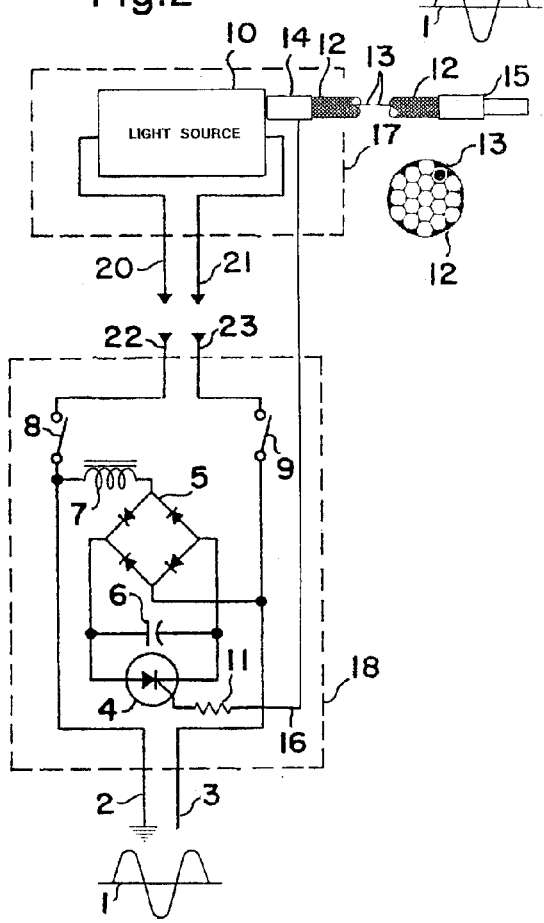
FIG. 2 shows the circuit enclosed within its own enclosure and adapted to be connected between the power source and the light source so that it may be supplied as an attachment. An external sensor lead connects to the proximal terminal of the cable.

FIG. 2 depicts the circuit in its own enclosure 18 and adapted to control the current to the light control 10 in enclosure 17 as an attachment. FIG. 2 shows the circuit as it might be used to modify existing equipment. The line-cord plug of light source 10 makes plug-in contact of its power conductors 20 and 21 with the respective power conductors 22 and 23 of the circuit to effect control in the same manner as the arrangement in FIG. 1. Arrowhead shapes are used to indicate plug and socket connections. Details of standadized plug and socket devices are omitted. Sensor lead 16 now includes an external and preferably flexible length that is adapted for connection to the proximal terminal 14 of fiberoptics cable 12.

Figure 3:
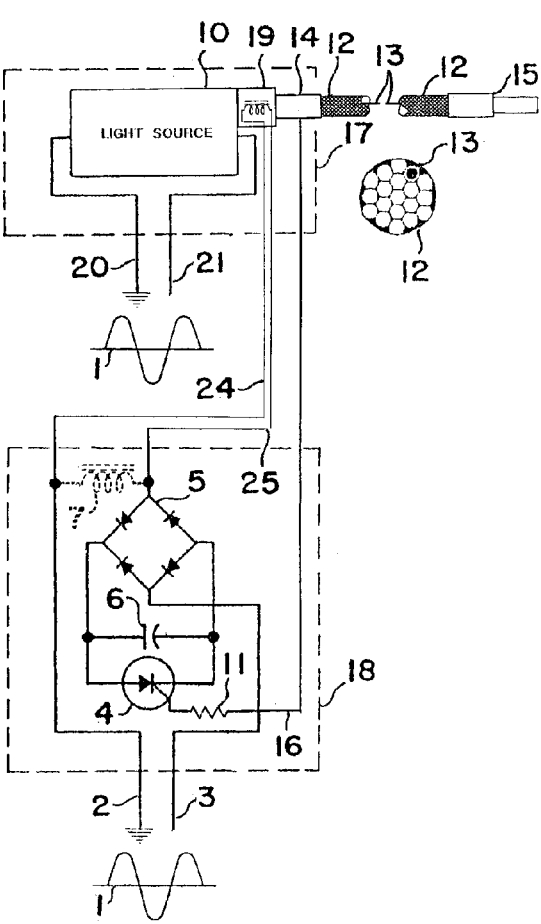
FIG. 3 shows the circuit with an electromagnetic or otherwise electrically actuated light blocking device employed as an alternative to the current connecting and interrupting contacts of the relay shown in FIG. 1. This arrangement does not interrupt current to the light source and the proximity control is therefore shown as independently connected to the power source and not connected between the light source and the power source.

FIG. 3 depicts another modification of the circuit designed to be attached to existing equipment, in which the coil 7 which closed relay contacts 8 and 9 in FIGS. 1 & 2 when energized (now shown in broken lines) has been moved. It is now part of a light blocking means 19, located between light source 10 and the proximal terminal 14 of fiberoptics cable 12, that interrupts the transmission of light from light source 10 rather than interrupting its power. Since power is not to be interrupted in this modification, light source 10 in enclosure 17 and the proximity control circuit in enclosure 18 are independently and individually connected to the power source 1. In addition to the external sensor lead 16 also described shown in FIG. 2, there are two external and typically flexible leads 24 and 25 which are connected to carry energizing current to the coil in light blocking means 19.

While the light blocking means is shown as actuated electromagnetically by coil 7 and thus made comparable comparable to the manner in which a relay is actuated, it should be understood that the description of light blocking means 19 is meant to include other electrically energized blocking means as well, such as liquid crystal devices.

While the invention has been described with respect to certain specific embodiments, it will be appreciated that many modifications and changes may be made by those skilled in the art, without departing from the true spirit of the invention. It is intended therefore, by the appended claims, to cover all such modifications and changes as fall within the true spirit and scope of the invention.

What is claimed as new and what is desired to secure by Letters Patent of the United States is:

1. In a device including a light source and a fiberoptics cable for transmission of light emissions, having electrically conductive proximal and distal terminals, the improvement comprising a proximity circuit reacting to earth ground capacitance influence and controlling said emissions, said circuit having a proximity sensing lead connnected to said proximal terminal and conductive means included with said cable to electrically interconnect said proximal and distal terminals.

2. The improvement as defined in claim 1, in which said light source is electrically powered and said control of said emissions is effected by a relay having contacts that control electric power said light source.

3. The improvement as defined in claim 1, in which said control of said emissons is effected by an electrically actuated means that blocks and unblocks said emissions.

4. The improvement as defined in claim 1, in which said proximity circuit comprises a silicon controlled rectifier having a sensitive gate resistively coupled to said sensing element, said controlled rectifier having its anode and cathode connected in parallel with a capacitor to the direct current output of a rectifier bridge that is adapted for connection the an alternating current source.

5. The improvement as defined in claim 4, in which the said sensitive gate has a maximum lgt of 200 microamperes.

6. A light source adapted to transmit emissions through a fiberoptics cable, said cable including conductive proximal and distal terminals which are electrically connected by a conductor included along said cable, and a proximity circuit having a proximity sensing element connected to said proximal terminal, said circuit controlling said emissions from the said distal terminal, permitting said emissions from said distal terminal of said cable when said circuit is energized by earth-ground capacitive influence and preventing said emissions when not energized.

7. The light source as defined in claim 6, in which the proximity circuit comprises a thyristor having a sensitive gate resistively coupled to a sensing element, said thyristor being connected in parallel with a capacitor to the direct current output of a rectifier bridge which is adapted for connection to an alternating current source.

8. The light source as defined in claim 7, in which the said thyristor is a controlled rectifier.

9. The light source as defined in claim 7, in which the sensitive gate has a maximum lgt of 200 microamperes.

10. The light source as defined in claim 7, in which said light source is electrically powered and said control of emissions is effected by the proximity circuit control of a relay having contacts that control power to said light source.

11. The light source as defined in claim 7, in which said control of emissions is effected by the proximity circuit control of an electrically actuated means that blocks and and unblocks said emissions.

\* \* \* \* \*